United States Patent
Adda

(10) Patent No.: US 6,410,803 B1
(45) Date of Patent: *Jun. 25, 2002

(54) PROCESS FOR THE PREPARATION OF PARA-FLUOROPHENOL

(75) Inventor: Michel Adda, Kfar-Saba (IL)

(73) Assignee: Bromine Compounds Limited, Beer Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/462,281

(22) PCT Filed: May 28, 1998

(86) PCT No.: PCT/IL98/00248

§ 371 (c)(1),
(2), (4) Date: Jan. 5, 2000

(87) PCT Pub. No.: WO99/02473

PCT Pub. Date: Jan. 21, 1999

(30) Foreign Application Priority Data

Jul. 7, 1997 (IL) .................................................. 121253

(51) Int. Cl.$^7$ .............................................. C07C 39/24
(52) U.S. Cl. ...................... 568/775; 568/774; 568/778
(58) Field of Search ................................ 568/775, 777, 568/778

(56) References Cited

U.S. PATENT DOCUMENTS 2,934,569 A * 4/1960 Kuehlewind ................ 569/775
2,950,325 A   8/1960 Britton et al.
6,037,503 A * 3/2000 Oren ........................... 568/777

FOREIGN PATENT DOCUMENTS

| DE | 3430554 | 2/1986 |
| GB | 850 888 | 10/1960 |
| JP | 06 211716 | 8/1994 |
| SU | 143404 | 1/1962 |
| WO | WO 97/266235 | 7/1997 |

OTHER PUBLICATIONS

M.M. Boudakian, et al.: Aromatic Fluorine . . . P–Bromofluoerobenzene, Journal of Organic Chemistry, vol. 26, No. 11, Nov. 1961, pp. 4641–4645, XP002030172.

* cited by examiner

Primary Examiner—Michael L. Shippen
(74) Attorney, Agent, or Firm—Anderson Kill & Olick; Eugene Lieberstein; Michael N. Meller

(57) ABSTRACT

A method for the preparation of p-fluorophenol by the alkaline hydrolysis of p-bromofluorobenzene in the presence of a copper-containing catalyst at an elevated temperature under pressure, the alkaline agent being a strong base, characterized in that said p-bromofluorobenzene, copper-containing catalyst and strong base are contacted with water where at least the base is gradually added to the reaction zone at an essentially uniform flow rate such that the addition of the base lasts at least the time required to complete the reaction in a batch operation, and less than 12 hours, and the molar ratio of the base is between 1.8 to 3 with respect to said p-bromofluorobenzene.

16 Claims, No Drawings

PROCESS FOR THE PREPARATION OF PARA-FLUOROPHENOL

FIELD OF THE INVENTION

The present invention relates to the preparation of p-fluorophenol by alkaline hydrolysis of p-bromofluorobenzene.

BACKGROUND OF THE INVENTION

One of the major synthetic routes for the preparation of p-fluorophenol, a substance of great commercial importance as an intermediate for various agrochemicals and pharmaceuticals, involves the alkaline hydrolysis of p-bromofluorobenzene in the presence of a copper catalyst. However, the hydrolysis reactions taught in the art are accompanied by the formation of considerable amounts of phenol and other by-products such as difluorodiphenylether and fluorohydroxydiphenylether, the latter two being formed by coupling. The formation of the phenol is particularly problematic, since it cannot be separated from p-fluorophenol by distillation.

The art has attempted to obtain p-fluorophenol in high yields, and simultaneously, to reduce the amounts of the phenol by-product formed during the alkaline hydrolysis of p-bromofluorobenzene, by appropriate selection of the alkaline agents. Boudakian et al., JOC 26, p. 4641 (1961), reported that the use of strong bases such as NaOH had yielded poor results, this reference indicating that calcium hydroxide is a superior base for the hydrolysis. This approach is further supported by U.S. Pat. No. 2,950,325, which suggests using alkaline earth metal oxides or hydroxides, explaining that the phenol by-product tends to form when a strong base, e.g., NaOH or KOH, is employed in the reaction, and also by GB 850,888, which presents unsatisfactory results when NaOH is used as the alkaline agent in the hydrolysis, compared with $Ca(OH)_2$.

The applications of other bases, such as $NaHF_2$ or $Ba(OH)_2$, were disclosed in Russian Patent No. 143404 and DE 3430554, respectively.

In conclusion, the art has taught avoidance of the use of strong bases as the alkaline agents in the preparation of p-fluorophenol via the hydrolysis of p-bromofluorobenzene, as they lead to a high degree of phenol contamination. The use of a weak base like $Ca(OH)_2$, effectively permits reduction of the formation of phenol but the p-fluorophenol is obtained in a yield of 50 to 70% and large amounts of by-products are formed.

In a copending patent application, International Patent Application No. PCT/IL97100019, it is suggested using a mixture of NaOH and $Na_2CO_3$, which has been found to improve the efficiency of the hydrolysis reaction, providing high yields of the p-fluorophenol while reducing the level of the phenol, to even below 0.1%.

It is an object of the present invention to provide a process for preparing p-fluorophenol via the alkaline hydrolysis of p-bromofluorobenzene, where a strong base is used alone, which gives the product in high yields, contaminated by only low amounts of the phenol, the content of this undesired by-product being in the order of 0.1% or less.

It is another object of the present invention to provide such a process which is industrially advantageous, as it allows high reactor productivity and easy recovery of the product with a minimal amount of waste.

SUMMARY OF THE INVENTION

It has now been found that it is possible to carry out the alkaline hydrolysis of p-bromofluorobenzene in the presence of copper-containing catalysts, to give p-fluorophenol, while employing as the alkaline agent a strong base such as NaOH or KOH solely, and—contrary to what is taught in the art—to obtain p-fluorophenol in high yields while reducing the phenol by-product contamination to a very low level.

The present invention provides a method for the preparation of p-fluorophenol by the alkaline hydrolysis of p-bromofluorobenzene in the presence of a copper-containing catalyst at an elevated temperature under pressure, the alkaline agent being a strong base, characterized in that said p-bromofluorobenzene, copper-containing catalyst and strong base are contacted with water and where at least the base is gradually added to the reaction zone at an essentially uniform flow rate such that the addition of the base lasts at least the time required to complete the reaction in a batch operation, and less than 12 hours, and the molar ratio of the base is between 1.8 to 3 with respect to said p-bromofluorobenzene.

In such an operating mode, the strong base is assumed to be fed into the reaction zone at a rate similar to the reaction rate, thereby avoiding the build up of a high concentration of said strong base in the reaction zone, to which the phenol formation is believed to be attributed. However, regardless of the exact explanation, the fact is that operating in the above described mode yields the desired results which the prior art failed to achieve. By the term "the time required to complete the reaction in a batch operation" is meant the time required to complete a reaction where all the reactants, i.e., the p-bromofluorobenzene, the water, the catalyst and the strong base, are stationary reaction phases. By the term "stationary reaction phase" is meant a. reaction component which is stationary from a point of view outside the reaction zone, said component being fixed within said reaction zone, ie., no flow of this component in or out of the reaction zone occurs, even though of course there may be relative motion of these components within said reaction zone.

According to the present invention, the gradual addition of the strong base to the reaction zone lasts at least the time that would have been required to complete the reaction in a batch operation, which is a well known reaction in the art, and is typically between 2 to 5 hours, and accordingly, the gradual addition of the strong base according to the present invention preferably lasts between 2 to 12 hours. Anyway, the time required to complete the reaction in a batch operation can be evaluated by monitoring the amount of the product, p-fluorophenol, and determining when this amount becomes constant after having increased during the course of the batch reaction.

Surprisingly, the above described mode of operation, wherein at least one of the reactants—the strong base—is not a stationary reaction phase as herein defined, has succeeded, even though a strong base is used, in producing high yields of a very pure p-fluorophenol, accompanied by only minor amounts of phenol by-product, the content of which is about 0.1% and even less. The prior art has only taught employment of a strong base in a batch operation, as explained hereinbefore, and has failed to give satisfactory results for the hydrolysis.

The addition rate specified above is the rate of gradual addition of the strong base to the reaction apparatus previously charged with water, copper catalyst and p-bromofluorobenzene, wherein the water, the copper catalyst and the p-bromofluorophenol are stationary reaction phases as defined herein before. However, it should be understood that according to the present invention, the p-bromofluorobenzene and/or the copper-containing catalyst may not be stationary reaction phases, and they can be introduced in a progressive manner to the reaction zone by feeding them thereto over a certain period of time. One skilled in the art will be able to calculate the flow conditions and to adjust the flow of the strong base into the reaction apparatus in order to maintain the optimal level of the strong base.

The reaction is carried out at temperatures from 180° to 220° C., and preferably at a temperature in the range between 190° to 210° C., under pressure. The strong base according to the present invention is preferably NaOH or KOH, NaOH being usually preferred due to economic considerations. The base is preferably provided as an aqueous solution, the concentration by weight of which varies from 20% to 50%. As indicated above, the molar ratio between the strong base and the p-bromofluorobenzene varies between 1.8 to 3.0.

The copper-containing catalyst according to the present invention is either in the cuprous or cupric oxidation state, and is preferably selected from among $Cu_2O$, CuO and $CuSO_4.5H_2O$, the most preferred being $Cu_2O$. The molar ratio of p-bromofluorobenzene/catalyst may vary in the range between 1 to 15.

DETAILED DESCRIPTION OF PREFERRED EMBODIMENTS

In a preferred embodiment of the present invention, p-bromofluorobenzene and the copper-containing catalyst, in a molar ratio in the range between 1 to 15, are charged into a pressure reactor together with water. The amount of p-bromofluorobenzene is preferably between 16% to 55% by weight and preferably between 27% to 49% of the final content of all reactants, i.e., upon complete addition of the strong base which is to follow and including the copper-containing catalyst. Water is added to 100%.

When the copper-containing catalyst is $Cu_2O$, the molar ratio of p-bromofluorobenzene/$Cu_2O$ varies between 2 to 15, and preferably between 4 to 6, while when CuO or $CuSO_4.5H_2O$ are employed, the molar ratio between p-bromofluorobenzene and the catalyst varies between 1 to 8, and preferably between 2 to 4.

The hydrolysis according to the present invention is preferably conducted at an elevated temperature from about 180° to 220° C. The more preferred temperature range is from about 190° to 210° C. In general, while increasing the temperature enhances the reaction rate, it has the negative effect of producing larger amounts of the undesired phenol contamination, so operating at a temperature of about 200° to 205° C. is believed to be optimal. According to the present invention, the mixture charged in the pressure reactor, comprising the water, the catalyst and the p-bromofluorobenzene, is heated to a temperature in said range and is maintained at said temperature, under sufficient agitation to allow the aqueous phase and the organic phase to become dispersed, an agitation rate of about 800 rpm being appropriate, while an aqueous solution of the strong base having a weight concentration of about 20 to 50 percent, preferably about 45 percent, is allowed to flow continuously into the reactor, typically at a constant flow rate, preferably for more than 2 hours, and more preferably between 4 to 8 hours. An appropriate means of permitting the flow of the base solution into the reactor is a metering pump, but alternative means may as well be applied. It is evident from the data resulting from carrying out the preferred embodiments that increasing the addition time of the base will reduce the content of the phenol by-product. The preferred molar ratio between the total amount of the base and the p-bromofluorobenzene varies between 2 to 2.4.

In another variant of the present invention, upon completing the gradual addition of the base solution to the reactor, the reaction mixture is maintained at the above-indicated reaction temperature for an additional period of time, typically for about an hour, to allow the complete conversion of the p-bromofluorophenol.

The final concentration of the p-fluorophenol in the reactor varies between 10 to 30% (by weight), and it is recovered from the reaction mixture by conventional procedures. First, the mixture is cooled to about 70° C. and subsequent to the removal of the catalyst by filtration, the mixture is acidified to pH of about 3 to 7 and preferably around 5, and is cooled to room temperature. The reaction mixture is then extracted successively with an appropriate solvent, the solvent employed for this purpose being selected from among toluene, butyl acetate and methyl isobutyl ketone, where toluene or butyl acetate are preferred. The extracts are combined and subjected to fractional distillation on a 5–10 theoretic plates column. The p-fluorophenol comes of at 123–125° C. at 100 mm Hg.

All the above and other characteristics and advantages of the invention will be better understood through the following illustrative and non-limitative description of preferred embodiments thereof.

EXAMPLE 1

An 8-liter pressure reactor was filled with 1952 g water, 1847 g p-bromofluorobenzene (10.55 mole) and 369 g $Cu_2O$ catalyst (2.58 mole). The agitation rate was 800 rpm. The mixture was heated to 205° C. Once this temperature was attained, 2063 g NaOH 45% (a molar ratio of 2.2:1 with regards to the p-bromofluorobenzene) was added to the reactor, at a constant flow rate, over 7 hours, the temperature being maintained at 205° C. At the end of the addition of the NaOH solution, the product mixture was cooled to 70° C. to remove the catalyst. The filtrate was acidified to pH=5 with 1147 ml HCl 32% and cooled to ambient temperature. The product distribution of the acidified mixture was as follows (GC area%): p-fluorophenol: 97.2%, phenol: 0.09%, unreacted p-bromofluorophenol: 0.2%, fluorobenzene: 0.15%, 4,4"-difluorodiphenyl ether: 1.5% and 4-fluoro-4"-hydroxydiphenyl ether: 0.8%.

The product was extracted twice with 2000 ml of toluene. The two extracts were mixed together. The mixture was distilled fractionally in a 7 plates distillation column. The solvent was distilled at atmospheric pressure and can be recycled. The distillation is then operated at 100 mm Hg. An intermediate fraction of 260 gr containing 58 gr of p-fluorophenol is collected and may be recycled to the next distillation. The main fraction containing 946 gr of p-fluorophenol of 99.8 purity with less than 0.1% phenol. The calculated yield of p-fluorophenol is of about 85% based on the starting p-bromofluorobenzene.

EXAMPLES 2–7

The same operations as in Example 1 are carried out in the following examples with the same NaOH to p-bromofluorobenzene molar ratio of 2.2:1, but with the amounts of reagents and catalyst and composition of the acidified product mixture according to the following table.

TABLE I

| Ex. | Temp. (° C.) | Addition time (hr) | PBFB loading (wt %) | PBFB/Cu₂O weight ratio | product distribution (area %) | | |
|-----|------|--------|-----|-------|-----------|-------|--------|
| | | | | | p-fluoro phenol | Phenol | Others |
| 2 | 200 | 4(+1*) | 29 | 5 | 99.2 | 0.11 | 0.7 |
| 3 | 200 | 6 | 29 | 5 | 96.3 | 0.09 | 2.8 |
| 4 | 205 | 6 | 29 | 5 | 96.0 | 0.11 | 2.9 |
| 5 | 200 | 7 | 29 | 3.3 | 97.1 | 0.07 | 2.8 |
| 6 | 195 | 6(+1*) | 42 | 5 | 98.5 | 0.12 | 1.4 |
| 7 | 200 | 5 | 29 | 5** | 97.8 | 0.12 | 2.1 |

PBFB = p-bromofluorobenzene
*additional heating after NaOH addition
**CuO instead of Cu₂O as catalyst While embodiments of the invention have been described by way of illustration, it will be apparent that the invention can be carried out by persons skilled in the art with many modifications, variations and adaptations, without departing from its spirit or exceeding the scope of the claims. For example, minor amounts of weak bases may be present initially in the reactor or may be provided gradually together with the strong base, or the progressive addition of the base could be done at a rate which is not necessarily constant, as the rate may slightly vary during the reaction.

What is claimed is:

1. A method for the preparation of p-fluorophenol by the alkaline hydrolysis of p-bromofluorobenzene in the presence of a copper-containing catalyst at an elevated temperature under pressure, the alkaline agent being a strong base, wherein said p-bromofluorobenzene, copper-containing catalyst and strong base are contacted with water where at least the base is gradually added to the reaction zone at an essentially uniform flow rate such that the addition of the base lasts at least the time required to complete the reaction in a batch operation, and less than 12 hours, and the molar ratio of the base is between 1.8 to 3 with respect to said p-bromofluorobenzene.

2. A method as in claim 1, wherein the gradual addition of the base lasts between 2 to 12 hours.

3. A method as in claim 1, wherein the base is selected from the group consisting of NAOH and KOH.

4. A method as in claim 3, wherein the molar ratio of the base/p-bromofluorobenzene is between 2 to 2.4.

5. A method as in claim 4, wherein the base is NaOH.

6. A method as in claim 1, wherein the base is provided in aqueous solution having a weight concentration between 20 to 50%.

7. A method as in claim 1, wherein the copper-containing catalyst is selected from the group consisting of $Cu_2O$, CuO and $CuSO_4 \cdot 5H_2O$.

8. A method as in claim 6, wherein between about 1 to 15 moles of p-bromofluorobenzene are used per mole of catalyst.

9. A method as in claim 7, wherein the copper-containing catalyst is $Cu_2O$ and the molar ratio of p-bromofluorobenzene to said catalyst is between 4 to 6.

10. A method as in claim 1, wherein the gradual addition of the base to the reaction zone lasts about 4 to 8 hours.

11. A method as in claim 1, wherein the reaction zone is a pressure reactor provided with means for introducing the base thereto.

12. A method as in claim 1, wherein the reaction is carried out a temperature in the range between 180° to 220° C.

13. A method as in claim 12, wherein the reaction temperature is between 190° to 210° C.

14. A method as in claim 1, wherein the copper-containing catalyst is removed from the reaction mixture, and the p-fluorophenol is recovered from said reaction mixture by acidification thereof followed by extraction with a suitable solvent and distillation.

15. A method as in claim 14, wherein the solvent is selected from the group consisting of toluene and butylacetate.

16. A method as in claim 8, wherein the copper-containing catalyst is $Cu_2O$ and the molar ratio of p-bromofluorobenzene to said catalyst is between 4 to 6.

* * * * *